United States Patent [19]

Fabry et al.

[11] Patent Number: 5,041,597

[45] Date of Patent: Aug. 20, 1991

[54] SURFACE-ACTIVE SULFOPHOSPHORIC-ACID-(PARTIAL)-ALKYL-ESTERS

[75] Inventors: Bernd Fabry, Korschenbroich; Hans-Herbert Friese, Monheim; Friedrich Pieper, Langenfeld; Guenter Uphues, Monheim, all of Fed. Rep. of Germany

[73] Assignee: Henkel Kommanditgesellschaft auf Aktien, Duesseldorf-Holthausen, Fed. Rep. of Germany

[21] Appl. No.: 529,768

[22] Filed: May 25, 1990

Related U.S. Application Data

[63] Continuation of Ser. No. 304,389, Jan. 30, 1989, abandoned.

[30] Foreign Application Priority Data

Jan. 30, 1988 [DE] Fed. Rep. of Germany ....... 3802815

[51] Int. Cl.$^5$ .................. C07B 45/02; C07F 9/09; C07C 309/08; C07C 309/10
[52] U.S. Cl. .................................. 558/177; 558/183; 558/186
[58] Field of Search ............... 558/148, 177, 183, 186

[56] References Cited

U.S. PATENT DOCUMENTS 3,484,474 12/1969 Krause ........................... 260/459
4,102,911 7/1978 Majima et al. .................. 260/400

FOREIGN PATENT DOCUMENTS 498872 12/1970 Switzerland.

OTHER PUBLICATIONS

Maurer et al.; J. Am. Oil Chem. Soc. 41, 205 (1964), pp. 205–208.
C. Herranz; J. Am. Oil Chem. Soc. 64, 1038 (1987).
A. J. Olenick, W. C. Smith; Soap, Cosm. Chem. Spec. 7, 26 (1986).
Acta Polym. 38, 5 (1987).
Chemische Technologie, Bd. 7, pp. 123–132 (1986).
Chemische Technologie, vol. 7, pp. 123 ff, 131–132, Carl-Hanser-Verlag, Muenchen-Wien (1986).
Kirk-Othmer, Encyclopedia of Chemical Technology, Third Edition, vol. 22, pp. 359–363 (1983).
"Surface-Active Ethylene Oxide Adducts", N. Schoenfeldt, Pergamon Press, First English Edition (1969), pp. 655–658.

Primary Examiner—Mary C. Lee
Assistant Examiner—Michael G. Ambrose
Attorney, Agent, or Firm—Ernest G. Szoke; Wayne C. Jaeschke; Real J. Grandmaison

[57] ABSTRACT

The invention concerns a process for the manufacture of surface-active sulfophosphoric-acid-(partial)-alkyl-esters and their alkali-, alkaline earth-, ammonium- and amine salts by the sulfonation of phosphoric acid esters and subsequent hydrolysis of the sultone intermediate stages formed.

18 Claims, No Drawings

SURFACE-ACTIVE SULFOPHOSPHORIC-ACID-(PARTIAL)-ALKYL-ESTERS

This application is a continuation of application Ser. No. 304,389, filed on Jan. 30, 1989, now abandoned.

BACKGROUND OF THE INVENTION

1. Field of the Invention

This invention relates to a process for the manufacture of surface-active sulfophosphoric-acid-(partial)-alkyl-esters and their alkali-, alkaline earth-, ammonium- and/or amine salts by the sulfonation of phosphoric acid esters and the subsequent hydrolysis of the sultone intermediate stages.

2. Description of the Related Art

Although the use of phosphates and phosphonates as builders in detergent recipes is well known, the use of phosphoric compounds as surfactant is much less common.

The synthesis of surfactants containing phosphorus through the reaction of saturated alpha-bromo-fatty acid esters with triethylphosphite is disclosed by Maurer et. al. in J. Am. Oil Chem. Soc. 41, 205 (1964). Such alpha-phosphono-fatty acid esters have only average surface-active properties. The manufacture of alkyl phosphinates by the reaction of alpha-olefins with phosphorous or hypophosphorous acids is also known as disclosed by C. Herranz in J. Am. Oil Chem. Soc. 64, 1038 (1987). These substances also have only moderate washing and foaming properties.

Phosphoric acid esters with P-O-C-bonds have clearly improved surfactant properties as compared with the surfactants described by Maurer and Herranz, in which phosphorus is directly linked with a carbon chain. It is known, for example, that alkyl phosphates can be used as wetting agents, antistatic agents, emulsifying agents and as detergents and cleaning agents as disclosed by A. J. Olenick, W. C. Smith in Soap, Cosm. Chem. Spec. 7, 26 (1986). However, these substances have only a slight foaming capacity and they are less resistant to hard water. Some are poorly soluble in water.

The use of alkyl phosphates as antistatic agents for synthetic fibers is also known, as disclosed in Acta Polym. 38, 5 (1987). These materials are manufactured by the reaction of alcohols or alcohol-polyoxy-alkyl-ethers with $POCl_3$.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The present invention provides long-chain alkyl phosphates having improved surface-active properties, improved water solubility and improved resistance to hard water. The invention is based on the surprising discovery that phosphoric-acid-(partial)-alkyl-esters containing sulfonate groups are distinguished by clearly improved surfactant properties, better water solubility and an improved resistance to hard water.

The invention provides a process for the manufacture of surface-active sulfophosphoric-acid-(partial)-alkyl-esters and their alkali-, alkaline earth-, ammonium- and/or amine salts, wherein unsaturated alkyl, unsaturated alkyl/unsaturated alkyl-polyoxy-alkyl- and/or unsaturated alkyl-polyoxy-alkyl-phosphoric acid esters of the general formula I:

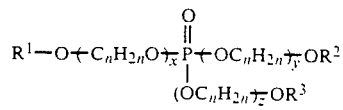

are reacted with $SO_3$ and the reaction products are hydrolyzed with aqueous solutions of 1 to 1.5 mol of alkalihydroxides, alkaline earth hydroxides, ammonium hydroxides, amines or anhydrous amines per mole of combined $SO_3$.

In formula I, the radical $R^1$ signifies an alkenyl group with 8 to 24 carbon atoms, the radicals $R^2$ and $R^3$ are the same or different and signify hydrogen or an alkenyl group with 8 to 24 carbon atoms, n is a number from 2 to 4, the subscripts x, y and z are the same or different and signify a number from 0 to 30.

Sulfophosphoric-acid(partial)-alkyl-esters with particularly favorable surface-active properties are obtained by sulfonation of formula I compounds wherein the radical $R^1$ signifies an alkenyl group with 12 to 24 carbon atoms, the radicals $R^2$ and $R^3$ are the same or different and signify hydrogen or an alkenyl group with 12 to 24 carbon atoms, $n=2$, and the subscripts x, y, and z are the same or different and signify a number from 0 to 10. More preferably, as educts such phosphoric acid esters of formula I are used in which $R^1$ signifies an alkenyl group with 16 to 22 carbon atoms or a fatty alkyl group consisting predominantly of oleyl-, palmitoleyl-, linoleyl-, gadoleyl- and/or erucyl groups, and the radicals $R^2$ and $R^3$ are the same or different and signify hydrogen or an alkenyl group with 16 to 22 carbon atoms or a fatty alkyl group consisting predominantly of oleyl, palmitoleyl-, linoleyl-, gadoleyl- and/or erucyl groups.

The sulfonation of the compounds of general formula I is preferably carried out at temperatures between 20° and 80° C., and more preferably at temperatures between 30° and 50° C. The sulfonation may be carried out using sulfuric acid, oleum or gaseous mixtures containing $SO_3$, and preferably using gaseous mixtures containing $SO_3$. The $SO_3$ content of these gaseous mixtures of $SO_3$ and air or inert gases such as nitrogen is preferably between 1 and 10 volume percent. The molar ratio of the double-bond equivalents in the educt (phosphoric acid ester) with respect to $SO_3$ preferably lies between 100:5 and 100:180, most preferably between 100:5 and 100:130.

The sulfonation reactions with sulfur trioxide may be carried out either continuously or discontinuously and in the usual reactors conventionally used for the sulfating of fatty alcohols or the sulfonation of fatty acid esters, alkyl benzols or olefins. Preferred reactors are of the "fall film" reactor type, such as disclosed by Kirk-Othmer, Encyclopedia of Chemical Terminology 22. 28 ff (1983).

After the sulfonation reaction, the reaction mixture is hydrolyzed with an aqueous solution of alkali hydroxides, alkaline earth hydroxides, ammonium hydroxide or amines or mixtures thereof or with anhydrous amines. The reaction mixture may be added to the aqueous base solution or the anhydrous amine, or the aqueous base solution or the anhydrous amine may be added to the reaction mixture. Preferably the crude sulfonation product is added to the aqueous base solution whereby preferably 1 to 1.5 mol. of hydroxide and/or amine is used per mole of combined sulfur trioxide. The hydroxides or amines serve to hydrolyze and neutralize the sulfonation product. Excess hydroxide or amine is generally necessary to neutralize the gaseous $SO_3$ dissolved in the sulfonation product and to catalyse the subsequent hydrolysis. Sodium hydroxide, ammonium hydroxide, diethanolamine, triethanolamine or mixtures thereof are preferably used as neutralization bases. The concentration of the hydroxides or amines in water is preferably selected such that the end product forms an aqueous solution which will still flow and be pumpable.

The sulfonation reaction gives rise to isomerization of the unsaturated alkyl-, unsaturated alkyl/unsaturated alkylpolyoxyalkyl- and/or unsaturated alkyl-polyoxyalkyl-phosphorus-acid-esters of formula I, resulting in a statistical distribution of the position of the olefin double-bonds along the alkenyl group. During the reaction of $SO_3$ with the olefin double-bonds, 1,2-sultones are probably initially formed, which isomerize very rapidly to 1,3-sultones and more slowly to 1,4-sultones, and at higher temperatures also to unsaturated sulfonic acids. To convert the sultones first formed in the sulfonation into hydroxy sulfonates, it is necessary to subject the sulfonation products to a hydrolysis wherein the reaction products are heated until there is complete destruction of the sultone groups which have been formed. The time required for this is dependent on pressure and temperature. For example, at 100° C. and under normal pressure, a complete hydrolysis to the hydroxy sulphonate can be achieved in 4 hours and in a considerably shorter time under pressure. Independent of the hydrolysis conditions, the resulting ester function is completely hydrolysis-stable, i.e. saponification products of the phosphoric acid esters used are not formed.

The mixtures of surface-active hydroxy sulfonates that are obtained in the process according to the invention contain compounds of general formula II:

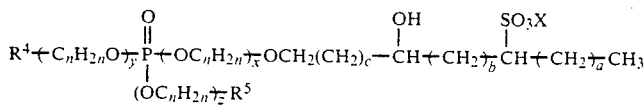

and of the formula III

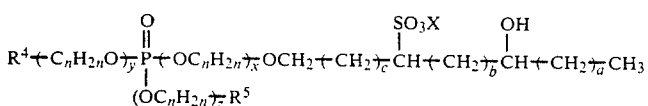

wherein $R^4$ and $R^5$ are the same or different and represent hydrogen,

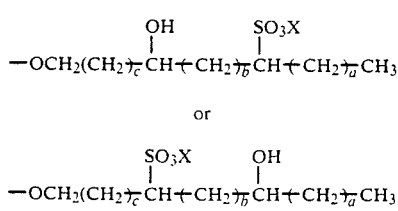

and further wherein X is selected from the group consisting of hydrogen, an alkali metal ion, an alkaline earth metal ion, an ammonium ion or an amine radical, n represents a number from 2 to 4, the subscripts x, y and z are the same or different and represent a number from 0 to 30, a and c represent a number from 0 to 18, b equals 0, 1 or 2, and the sum of a and b and c is a number between 4 and 20.

Accordingly, the invention also relates to mixtures of surface-active sulfophosphoric-acid-(partial)-alkyl-esters of the general formulae II and III.

The surface-active sulfophosphoric-acid-(partial)-alkyl-esters of the invention are formed as dark to light yellow alkaline solutions in the form of their alkali-, alkaline earth-, ammonium- and/or amine salts. If desired, these solutions can be bleached using hydrogen peroxide solutions or alkali hypochlorite solutions (Chlornatron) by treatment at 40° to 55° C. in a manner known in the art. The pH-value of these solutions can be adjusted to neutral using mineral and/or carboxylic acids, including hydrochlorid acid, sulfuric acid, phosphoric acid, citric acid, lactic acid, or mixtures thereof.

The unsaturated alkyl-, unsaturated alkyl/unsaturated alkylpolyoxyalkyl—and/or unsaturated alkyl-polyoxy-alkyl- phosphoric-acid-esters of general formula I may be synthesized according to processes known in the literature. They are derived from unsaturated alcohols having 8 to 24 carbon atoms having iodine numbers of between 10 and 150. Unsaturated alcohols with 12 to 24 carbon atoms are more preferred and particularly preferred are unsaturated alcohols with 16 to 22 carbon atoms, including oleyl alcohol or industrial alcohol cuts consisting predominantly of oleyl alcohol, palmitoleyl alcohol, linoleyl alcohol, gadoleyl alcohol and erucyl alcohol. In industrial alcohol cuts, small fractions of saturated alcohols such as cetyl- and stearyl alcohol are tolerable, particularly when the products manufactured therefrom are water-soluble. Particularly preferred are industrial cetyl/oleyl- and cetyl/linoleyl-alcohol cuts having iodine numbers between 70 and 110.

The oxalkylation of the unsaturated alcohols may be carried out using ethylene oxide, propylene oxide and-/or butylene oxide. The oxalkylations are known processes such as disclosed in "Chemische Technologie", Vol. 7, page 131–132, Carl-Hanser-Verlag, München-Wien (1986). The average degree of oxalkylation represented by x, y and z of the mixtures of homologous oxalkylates of formulas II and III corresponds to the molar quantity of combined alkylene oxides. The sulfo-phosphoric-acid(partial)alkyl-esters according to the invention of general formulas II and III preferably have degrees of oxalkylation between 0 and 10.

The phosphating of the unsaturated and optionally oxalkylated alcohols may be carried out according to known methods such as disclosed in Chemische Technologie, Vol. 7, page 123 ff, Carl-Hanser-Verlag, München-Wien (1986). For example, the unsaturated alcohols and/or unsaturated alcohol polyoxy-alkyl-ethers are reacted with phosphorus pentoxide or polyphosphoric acid. In this process, mixtures of mono-, di- and trialkyl derivatives are formed. When water entrainment agents are used, these partial ester mixtures may also be obtained directly using orthophosphoric acid. At reaction temperatures above 160° C. however, no classical esterification takes place. Instead, di- and polyphosphoric acids are primarily formed which react in a known manner with alcohols and/or alcohol-polyoxy-alkyl-ethers.

To manufacture high-pure mono-, di- and trialkyl-phosphoric-acid-esters, unsaturated alcohols and/or unsaturated alcohol-polyoxy-alkyl-ethers may be reacted with phosphorus oxychloride. This method is less preferred because of the high corrosion risk when phosphorus oxychloride is used.

The sulfophosphoric-acid-(partial)-alkyl-esters of general formulas II and III according to the invention have a high surface activity and good surfactant properties for industrial application. They have a high foam stability even in hard water and have proved to have good solubility in water despite their high molecular weight. Their marked stability in highly alkaline media, their emulsifying properties and their good textile wetting ability are particularly significant.

The following examples are illustrative of the invention. Examples 1 and 2 illustrate the synthesis of two different oleyl phosphates. The remaining examples illustrate the sulfonation and neutralization of these oleyl phosphates.

EXAMPLE 1

Manufacture of oleyl phosohate A 420 grams (1.5 mol.) of industrial oleyl alcohol which was present in a mixture with small proportions of cetyl-alcohol (HD-Ocenol ™ 80/85: iodine number 89, OH-number 205), was placed in a 1-liter three-neck flask provided with a stirrer and thermometer. At a temperature of 60° to 70° C., 71 grams (0.5 mol.) of phosphorus-pentoxide was introduced gradually over 2 hours using a powder dosing device protected against air moisture. After a two-hour post-reaction period at 70° C., 10 ml of water was added and the composition was stirred for a further 3 hours at 90° C.

490 grams of a dark-colored oil was obtained, which had the following characteristics:

| | |
|---|---|
| Monoester | 43.3% by weight |
| Diester | 38.4% by weight |
| Triester | 3.4% by weight |
| H$_3$PO$_4$ | 1.7% by weight |
| Free alcohol | 13.0% by weight |
| H$_2$O (according to Fischer) | 0.15% by weight |
| Iodine number | 74 |
| Average molecular weight | 451 |
| Double-bond equivalents per mol. of phosphate | 1.3 |

EXAMPLE 2

Manufacture of oleyl phosohate B

Using the same conditions as in Example 1, 420 grams (1.5 mol ) of industrial oleyl alcohol (HD-Ocenol ™ 90/95: iodine number 92, OH-number 206) was converted to oleyl phosphate. 500 grams of a dark-colored oil with the following characteristics was obtained:

| | |
|---|---|
| Monester | 43.9% by weight |
| Diester | 43.9% by weight |
| Triester | 1.9% by weight |
| H$_3$PO$_4$ | 0.9% by weight |
| Free alcohol | 9.8% by weight |
| H$_2$O (according to Fischer) | 0.03% by weight |
| Iodine number | 76 |
| Average molecular weight | 464 |
| Double-bond equivalents per mol. of phosphate | 1.3 |

EXAMPLE 3

Sulfonation with 30% excess SO$_3$ 255 grams (0.5 mol.) of oleyl phosphate A as made in Example 1 was placed in a 1-liter sulfonation flask with a mechanical stirrer, a gas-inlet tube and jacket-cooling and reacted at 35° C. with 68 grams (0.85 mol.) of SO$_3$, corresponding to a 30% excess with respect to the double-bond equivalents. The SO$_3$ was formed by heating from a corresponding quantity of oleum, diluted with nitrogen to a concentration of 5 vol. percent and introduced over 31 minutes into the phosphoric-acid-alkyl-ester, and the temperature of the reaction mixture was maintained by cooling at a temperature below 50° C. After the sulfonation, the reaction mixture was cooled at 10° C., stirred into a dilute solution of 40 grams (1 mol.) of NaOH in 700 ml of water and then hydrolysed for 4 hours on the steam bath at 95° to 100° C. After cooling to 20° C., the pH-value of the reaction mixture was adjusted to 7.0 by the addition of HCl-solution.

The product obtained had the following characteristics:

| | |
|---|---|
| Anion surfactant (two-phase titration method according to standard method DFG-H-III-10) | 16% by weight = 0.3 mval/g |
| Unsulfonated ingredients (DGF-G-III-6b) | 1% by weight |
| Na$_2$SO$_4$ | 1% by weight |
| Na$_3$PO$_4$ | <0.1% by weight |
| H$_2$O (according to Fischer) | 82% by weight |
| Total sulfur | 1.2% by weight |
| Average molecular weight | 539 |
| Klett color number | 135 |

The Klett color number was determined in all the sulfonated products after 30 minutes of bleaching with 5% by weight of a 35% hydrogen peroxide solution. The measurement was carried out at a concentration of 5% by weight of anion surfactant, pH 7 and using a 1-cm cuvette and a blue filter (400–465 u).

EXAMPLE 4

Sulfonation with 50% excess SO$_3$

Using the same method as in Example 3, 78 grams (0.98 mol.) of SO$_3$ corresponding to a 50% SO$_3$ excess with respect to the double-bond equivalents was introduced over 37 minutes into 225 grams (0.5 mol.) of oleyl phosphate A. The neutralization was carried out with 48 grams (1.2mol.) NaOH in 800 ml of water.

The product obtained had the following characteristics:

| | |
|---|---|
| Anion surfactant (DGF-H-III-10): | 14% by weight = 0.26 mval/g |
| Unsulfonated ingredients (DGF-G-III-6b): | 3% by weight |

-continued

| | |
|---|---|
| Na$_2$SO$_4$ | 4% by weight |
| Na$_3$PO$_4$ | <0.1% by weight |
| H$_2$O (according to Fischer) | 79% by weight |
| Total sulfur | 1.78% by weight |
| Average molecular weight | 549 |
| Klett color number | 246 |

EXAMPLE 5

Sulfonation at 70° C.

Example 3 was repeated except the sulfonation temperature was 70° C.

The product obtained had the following characteristics:

| | |
|---|---|
| Anion surfactant (DGF-H-III-10) | 15% by weight = 0.28 mval/g |
| Unsulfonated ingredients (DGF-G-III-6b) | 2% by weight |
| Na$_2$SO$_4$ | 2% by weight |
| Na$_3$PO$_4$ | <0.1% by weight |
| H$_2$O (according to Fischer) | 81% by weight |
| Total sulfur | 1.41% by weight |
| Average molecular weight | 539 |
| Klett color number | 538 |

EXAMPLE 6

Sulfonation of oleyl phosohate B

Using the same method as in Example 3, 232 grams (0.5 mol.) of oleyl phosphate B as made in Example 2 was reacted with 68 grams (0.85 mol.) of SO$_3$ corresponding to a 30% excess with respect to the double-bond equivalents.

The product obtained had the following characteristics:

| | |
|---|---|
| Anion surfactant (DGF-H-III-10): | 17% by weight = 0.31 mval/g |
| Unsulfonated ingredients (DGF-G-III-6b): | 1% by weight |
| Na$_2$SO$_4$ | 1% by weight |
| Na$_3$PO$_4$ | <0.1% by weight |
| H$_2$O (according to Fischer) | 81% by weight |
| Total sulfur | 1.30% by weight |
| Average molecular weight | 552 |
| Klett color number | 143 |

EXAMPLE 7

Hydrolysis and neutralization with ammonium hydroxide

Example 3 was repeated, except that the hydrolysis and neutralization reaction was carried out using 68 grams (1 mol.) of concentrated (25%) ammonium hydroxide solution in 200 ml of water in a closed apparatus under reflux.

The product obtained had the following characteristics:

| | |
|---|---|
| Anion surfactant (DGF-H-III-10) | 58% by weight = 1.10 mval/g |
| Unsulfonated ingredients (DGF-G-III-6b) | 5% by weight |
| Na$_2$SO$_4$ | 2% by weight |
| Na$_3$PO$_4$ | <0.1% by weight |
| H$_2$O (according to Fischer) | 35% by weight |
| Total sulfur | 4.01% by weight |
| Average molecular weight | 527 |
| Klett color number | 156 |

EXAMPLE 8

Sulfonation in the fall film reactor

In a continually operating fall film reactor, 1.8 kg (4.05 mol.) of oleyl phosphate A of Example 1 was treated with SO$_3$ in the molar ratio of phosphate to SO$_3$ of 1:1.3 at a throughput of 10 grams/minute. The crude sulfonation product was stirred continuously into concentrated sodium hydroxide solution and then hydrolyzed and treated as described in Example 3.

The product obtained had the following characteristics:

| | |
|---|---|
| Anion surfactant (DGF-H-III-10) | 44% by weight = 0.82 mval/g |
| Unsulfonated ingredients (DGF-G-III-6b) | 3% by weight |
| Na$_2$SO$_4$ | 3% by weight |
| Na$_3$PO$_4$ | <0.1% by weight |
| H$_2$O (according to Fischer) | 50 % by weight |
| Total sulfur | 3.38% by weight |
| Average molecular weight | 539 |
| Klett color number | 104 |

It is to be understood that the above described embodiments of the invention are illustrative only and that modifications throughout may occur to those skilled in the art.

We claim:

1. A process for producing an aqueous solution of surface-active sulfophosphoricacid(partial)-alkyl esters and alkali metal, alkaline earth, ammonium and amine salts thereof comprising:

a) providing a phosphoric acid ester having the formula:

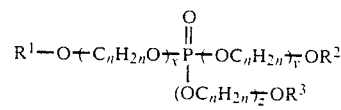

wherein R$^1$ represents an alkenyl group with 8 to 24 carbon atoms, the radicals R$^2$ and R$^3$ are the same or different and represent hydrogen or an alkenyl group with 8 to 24 carbon atoms, n is a number from 2 to 4, the subscripts x, y and z are the same or different and signify a number from 0 to 30;

b) sulfonating the product of step (a) with a sulfonation agent selected from the group consisting of sulfuric acid, oleum and a gaseous mixture containing SO$_3$; and c) subjecting the sulfonation product of step (b) to hydrolysis treatment in the presence of a base selected from the group consisting of alkali metal hydroxide, alkaline earth hydroxide, ammonium hydroxide and amine, said base being reacted in an amount of from about 1 to about 1.5 moles per mole of said sulfonation agent.

2. The process of claim 1 wherein said sulfonating agent comprises a gaseous mixture containing SO$_3$.

3. The process of claim 2 wherein the molar ratio of the double-bonds present in the phosphoric acid ester of step (a) with respect to SO$_3$ ranges from about 100 to about 5 up to about 100 to about 180.

4. The process of claim 3 wherein said molar ratio ranges from about 100 to about 5 up to about 100 to about 130.

5. The process of claim 2 wherein said gaseous mixture of $SO_3$ comprises a mixture of $SO_3$ gas and air or an inert gas, the $SO_3$ content of said gaseous mixture being within the range of from about 1 to about 10 volume percent.

6. The process of claim 5 wherein said sulfonation step (b) is conducted by heating the mixture to a temperature within the range of about 20 to about 80° C.

7. The process of claim 6 wherein said heating is conducted at a temperature of from about 30 to about 50° C.

8. The process of claims 1 or 2 wherein $R^1$ represents an alkenyl group having from 12 to 24 carbon atoms, $R^2$ and $R^3$ are the same or different and represent hydrogen or an alkenyl group having from 12 to 24 carbon atoms, n is 2 and x, y and z are the same or different and represent a number from 0 up to about 10.

9. The process of claim 8 wherein $R^1$ represents an alkenyl group having from 16 to 22 carbon atoms or the residuum of a fatty alkyl group predominantly selected from oleyl, palmitoleyl, linoleyl, gadoleyl, erucyl and mixtures thereof.

10. The process of claim 9 wherein $R^2$ and $R^3$ are the same or different and represent hydrogen, an alkenyl group having from 16 to 22 carbon atoms or the residuum of a fatty alkyl group predominantly selected from oleyl, palymitoleyl, linoleyl, gadoleyl, erucyl, and mixtures thereof.

11. The process of claim 10 wherein one or more of $R^1$, $R^2$ and $R^3$ are predominantly oleyl.

12. An aqueous solution of a mixture of surface-active sulfophosphoric-acid-partial-alkyl-esters having the formulas:

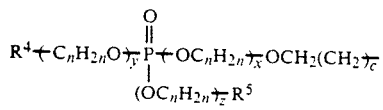

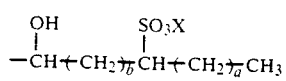

and

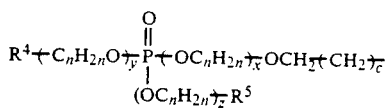

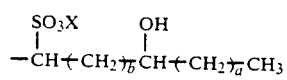

wherein the radicals $R^4$ and $R^5$ are the same or different and represent hydrogen,

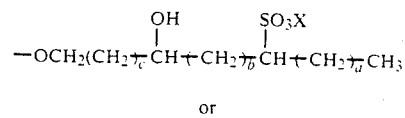

or

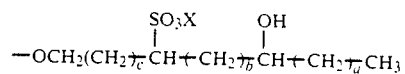

and further wherein X is selected from the group consisting of hydrogen, an alkali metal ion, an alkaline earth metal ion, an ammonium ion or an amine radical, n represents a number from 2 to 4, the subscripts x, y and z are the same or different and represent a number from 0 to 30, a and c represent a number from 0 to 18, b equals 0, 1 or 2, and the sum of a and b and c is a number between 4 and 20.

13. An aqueous solution of a mixture of surface-active sulfophosphoric acid mono-, di-, and tri-$C_{18}$-alkyl esters and alkali metal, alkaline earth metal, ammonium and amine salts thereof, prepared by sulfonating a phosphoric acid ester having the formula

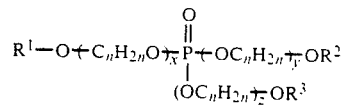

wherein $R^1$ represents an oleyl group, the radicals $R^2$ and $R^3$ are the same or different and represent hydrogen or an oleyl group, n is a number from 2 to 4, the subscripts x, y and z ar the same or different and signify a number from 0 to 30, with a sulfonating agent comprising a gaseous mixture containing $SO_3$, and subjecting the sulfonation product of hydrolysis in the presence of a base material selected from the group consisting of alkali metal hydroxide, alkaline earth hydroxide, ammonium hydroxide and amine, said base material being present in an amount of from about 1 to about 1.5 moles per mole of said sulfonating agent.

14. An aqueous solution as in claim 13 prepared by sulfonating said phosphoric acid ester with a gaseous mixture containing $SO_3$ wherein the molar ratio of the double bonds present in said phosphoric acid ester with respect to $SO_3$ ranges from about 100 to about 5 up to about 100 to about 180.

15. An aqueous solution prepared as in claim 13 wherein said gaseous mixture containing $SO_3$ comprises a mixture of $SO_3$ and air or an inert gas, and the $SO_3$ content of said gaseous mixture is from about 1 to about 10 percent by volume.

16. An aqueous solution as in claim 13 prepared by sulfonating said phosphoric acid ester at a temperature of from bout 20° to about 80° C.

17. An aqueous solution as in claim 13 prepared by sulfonating said phosphoric acid ester at a temperature of from about 30° to about 50° C.

18. An aqueous solution as in claim 13 wherein n is 2.